(12) United States Patent
Hurwitz

(10) Patent No.: US 12,714,366 B2
(45) Date of Patent: Aug. 25, 2026

(54) WEARABLE COMPUTING DEVICE TO ADJUST A CURRENT SUPPLIED TO A LIGHT SOURCE OF A SENSOR BASED ON AN AMOUNT OF AMBIENT LIGHT DETECTED BY ANOTHER SENSOR

(71) Applicant: Google LLC, Mountain View, CA (US)

(72) Inventor: Jonathan David Hurwitz, San Jose, CA (US)

(73) Assignee: GOOGLE LLC, Mountain View, CA (US)

( * ) Notice: Subject to any disclaimer, the term of this patent is extended or adjusted under 35 U.S.C. 154(b) by 3 days.

(21) Appl. No.: 18/855,276

(22) PCT Filed: Apr. 12, 2022

(86) PCT No.: PCT/US2022/024437
§ 371 (c)(1),
(2) Date: Oct. 8, 2024

(87) PCT Pub. No.: WO2023/200432
PCT Pub. Date: Oct. 19, 2023

(65) Prior Publication Data

US 2025/0248652 A1 Aug. 7, 2025

(51) Int. Cl.
*A61B 5/00* (2006.01)
*A61B 5/024* (2006.01)

(52) U.S. Cl.
CPC .......... *A61B 5/681* (2013.01); *A61B 5/02427* (2013.01); *A61B 5/02438* (2013.01);
(Continued)

(58) Field of Classification Search
CPC .... A61B 2560/0209; A61B 2560/0247; A61B 2562/0219; A61B 2562/0233;
(Continued)

(56) References Cited

U.S. PATENT DOCUMENTS

2014/0276119 A1* 9/2014 Venkatraman ..... A61B 5/02405 600/509
2017/0105682 A1 4/2017 MacDonald et al.
(Continued)

FOREIGN PATENT DOCUMENTS

CN 110141197 8/2019

OTHER PUBLICATIONS

Max30102, "High-sensitivity pulse oximeter and heart-rate sensor for wearable health". 2018 Maxim Integrated Products, Inc. (Year: 2018).*

(Continued)

*Primary Examiner* — Yi-Shan Yang
(74) *Attorney, Agent, or Firm* — DORITY & MANNING, P.A.

(57) ABSTRACT

A wearable computing device includes a body, a first sensor disposed at an upper part of the body, and a second sensor disposed at a lower part of the body. The first sensor detects ambient light in a surrounding environment of the wearable computing device and the second sensor includes one or more light sources and one or more detectors, the one or more light sources emitting light toward a body part of a user when the wearable computing device is worn by the user, and the one or more detectors receiving a reflection of the light emitted toward the body part to generate a signal indicating a biometric of the user. The wearable computing device further includes one or more processors which adjust a current supplied to the one or more light sources based on an amount of ambient light detected by the first sensor.

20 Claims, 8 Drawing Sheets

(52) U.S. Cl.
CPC .............. *A61B 5/721* (2013.01); *A61B 5/742* (2013.01); *A61B 2562/0233* (2013.01)

(58) Field of Classification Search
CPC ............ A61B 5/02427; A61B 5/02438; A61B 5/1118; A61B 5/681; A61B 5/6843; A61B 5/721; A61B 5/7221; A61B 5/742
See application file for complete search history.

(56) References Cited

U.S. PATENT DOCUMENTS

2017/0296075 A1 10/2017 Loseau et al.
2018/0156660 A1* 6/2018 Turgeon .................... G01J 1/44
2021/0161464 A1* 6/2021 Gowda ................ A61B 5/7267
2022/0108782 A1* 4/2022 Ahmed ................ A61B 5/7475
2023/0155078 A1* 5/2023 Chen ........................ G09G 3/20
345/207

OTHER PUBLICATIONS

International Preliminary Report on Patentability for PCT/US2022/024437, mailed on Oct. 24, 2024, 10 pages.
International Search Report and Written Opinion for PCT/US2022/024437, mailed on Dec. 9, 2022, 14 pages.

* cited by examiner

WEARABLE COMPUTING DEVICE TO ADJUST A CURRENT SUPPLIED TO A LIGHT SOURCE OF A SENSOR BASED ON AN AMOUNT OF AMBIENT LIGHT DETECTED BY ANOTHER SENSOR

PRIORITY CLAIM

This application is based upon and claims the right of priority under 35 U.S.C. § 371 to International Application No. PCT/US2022/024437 filed on Apr. 12, 2022. Applicant claims priority to and the benefit of International Application No. PCT/US2022/024437 and incorporates this application herein by reference in its entirety for all purposes.

FIELD

The disclosure relates generally to wearable computing devices. More particularly, the disclosure relates to wearable computing devices which adjust a current supplied to a light source of a sensor based on an amount of ambient light detected by another sensor.

BACKGROUND

Some wearable computing devices (e.g., wrist watches or fitness devices) can gather data regarding activities performed by the user, or regarding the user's physiological state. Such data may include data representative of the environment around the user or the user's interaction with the environment. For example, the data can include motion data regarding the user's movements and/or physiological data obtained by measuring various physiological characteristics of the user, such as heart rate, perspiration levels, and the like.

Some wearable computing devices have continuous heart rate monitoring in which an LED of a PPG sensor is active (i.e., emitting light) at all times during the day, but at the expense of power consumption which drains the battery of the wearable computing device. To mitigate the amount of power consumption, the brightness of the LED of the PPG sensor may be dimmed. Some wearable computing devices do not have continuous heart rate monitoring, but instead take a sample at predetermined time periods (e.g., every 10-15 min) or only have continuous heart rate monitoring if the user is exercising (e.g., during a workout) and drive the LEDs of the PPG sensor at a very high level during the times that the heart rate is being monitored. That is, the LEDs may be driven at a very high level because the LEDs are not being continuously driven throughout the day, but instead are only being utilized periodically or during a workout. Accordingly, there is a tradeoff between PPG sensor accuracy (e.g., driving a LED at a high level) and power consumption, as well as a tradeoff between PPG sensor availability/usage (continuous availability vs. periodic usage) and power consumption.

SUMMARY

Aspects and advantages of embodiments of the disclosure will be set forth in part in the following description, or can be learned from the description, or can be learned through practice of the example embodiments.

In an example embodiment, a wearable computing device is provided. The wearable computing device includes a body, a first sensor disposed at an upper part of the body, and a second sensor disposed at a lower part of the body. The first sensor is configured to detect ambient light in a surrounding environment of the wearable computing device and the second sensor includes one or more light sources and one or more detectors. The one or more light sources is configured to emit light toward a body part of a user when the wearable computing device is worn by the user, and the one or more detectors is configured to receive a reflection of the light emitted toward the body part to generate a signal indicating a biometric of the user. The wearable computing device further includes one or more processors which are configured to adjust a current supplied to the one or more light sources based on an amount of ambient light detected by the first sensor (i.e. dependent on an amount of ambient light detected by the first sensor, in particular dependent on a signal generated by the first sensor corresponding to the amount of ambient light detected by the first sensor).

In an embodiment, the second sensor includes a photoplethysmography (PPG) sensor configured to monitor a heart rate of the user when the wearable computing device is worn by the user. The one or more light sources includes one or more light-emitting diodes, and the one or more detectors includes one or more photodiodes.

In an embodiment, the wearable computing device further includes one or more inertial sensors disposed in the body. The one or more inertial sensors are configured to generate one or more motion signals based on a movement of the wearable computing device. The one or more processors are configured to adjust the current supplied to the one or more light sources based on the one or more motion signals generated by the one or more inertial sensors.

In an embodiment, the one or more processors are configured to execute one or more functions of the wearable computing device based on the location at which the force is applied to the display screen as determined by the one or more processors.

In an embodiment, the one or more processors are configured to increase the current supplied to the one or more light sources in response to the one or more motion signals generated by the one or more inertial sensors indicating a motion of the wearable computing device is of a predetermined type or is greater than a threshold value.

In an embodiment, the second sensor includes a photoplethysmography (PPG) sensor configured to monitor a heart rate of the user when the wearable computing device is worn by the user. The one or more light sources includes a plurality of light-emitting diodes, and the one or more detectors includes a plurality of photodiodes. When one or more motion signals generated by one or more inertial sensors indicate the lower part of the body of the wearable computing device is spaced apart from the body part of the user, the one or more processors are configured to cut off current supplied to at least one of the plurality of light-emitting diodes, and to increase current supplied to at least one other light-emitting diode of the plurality of light-emitting diodes.

In an embodiment, the one or more processors are configured to increase the current supplied to the one or more light sources in response to the amount of ambient light detected by the first sensor being greater than a threshold value.

In an embodiment, the wearable computing device further includes one or more inertial sensors disposed in the body of the wearable computing device. The one or more inertial sensors are configured to generate one or more motion signals based on a movement of the wearable computing device, and the one or more processors are configured to increase the current supplied to the one or more light sources if the amount of ambient light detected by the first sensor is greater than a first threshold value and the one or more motion signals generated by the one or more inertial sensors indicate a motion of the wearable computing device is of a predetermined type or is greater than a second threshold value.

In an embodiment, the wearable computing device further includes a display disposed at the upper part of the body of the wearable computing device. The display is configured to display biometric information. The first sensor includes an ambient light sensor disposed beneath the display, and according to another embodiment the ambient light sensor has a first sampling rate to detect the ambient light in a first operating mode of the wearable computing device, and has a second sampling rate to detect the ambient light in a second operating mode of the wearable computing device (the sampling rate corresponding to a number of detections per unit time).

In an embodiment, the one or more detectors are configured to detect ambient light in a space between the lower part of the body of the wearable computing device and the body part of the user. The one or more processors are configured to adjust the current supplied to the one or more light sources based on an amount of ambient light detected by the one or more detectors.

In an embodiment, the one or more processors are configured to determine a current value for which the current is to be adjusted to, according to one or more of a lookup table, a linear scaling method, and a nonlinear scaling method, using the amount of ambient light detected by the first sensor as an input.

In an example embodiment, a computer-implemented method is provided. The computer-implemented method includes detecting, by a first sensor disposed at an upper part of a body of a wearable computing device, ambient light in a surrounding environment of the wearable computing device, and adjusting, by one or more processors, a current supplied to one or more light sources of a second sensor based on an amount of ambient light detected by the first sensor. The second sensor is disposed at a lower part of the body of the wearable computing device and include the one or more light sources which emit light toward a body part of a user when the wearable computing device is worn by the user and one or more detectors which receive a reflection of the light emitted toward the body part to generate a signal indicating a biometric of the user.

In an embodiment, the method further includes generating, by one or more inertial sensors disposed in the body of the wearable computing device, one or more motion signals based on a movement of the wearable computing device. Adjusting, by the one or more processors, the current supplied to the one or more light sources of the second sensor, is based on the one or more motion signals generated by the one or more inertial sensors.

In an embodiment, the method further includes, in response to the one or more motion signals generated by the one or more inertial sensors indicating a motion of the wearable computing device is of a predetermined type or is greater than a threshold value, increasing the current supplied to the one or more light sources.

In an embodiment, the second sensor includes a photoplethysmography (PPG) sensor configured to monitor a heart rate of the user when the wearable computing device is worn by the user, the one or more light sources includes a plurality of light-emitting diodes, and the one or more detectors includes a plurality of photodiodes. In an embodiment method further includes, in response to one or more motion signals generated by one or more inertial sensors indicating the lower part of the body of the wearable computing device is spaced apart from a body part of the user, cutting off current supplied to at least one of the plurality of light-emitting diodes, and increasing current supplied to at least one other light-emitting diode of the plurality of light-emitting diodes.

In an embodiment, the method further includes generating, by one or more inertial sensors disposed in the body of the wearable computing device, one or more motion signals based on a movement of the wearable computing device, and increasing the current supplied to the one or more light sources to a peak value when the amount of ambient light detected by the first sensor is greater than a first threshold value and the one or more motion signals generated by the one or more inertial sensors indicate a motion of the wearable computing device is of a predetermined type or is greater than a second threshold value.

In an embodiment, the method further includes displaying, on a display of the wearable computing device, biometric information. The first sensor includes an ambient light sensor disposed below the display and detecting the ambient light by the first sensor includes sampling the ambient light at a first sampling rate in a first operating mode of the wearable computing device, and at a second sampling rate in a second operating mode of the wearable computing device.

In an embodiment, the method further includes detecting, by the one or more detectors, ambient light in a space between the lower part of the body and the body part of the user. Adjusting, by the one or more processors, the current supplied to the one or more light sources of the second sensor, is further based on an amount of ambient light detected by the one or more detectors.

In an embodiment, the method further includes determining, by the one or more processors, a current value for which the current is to be adjusted to, according to one or more of a lookup table, a linear scaling method, and a nonlinear scaling method, using one or more of the amount of ambient light detected by the first sensor, the amount of ambient light detected by the one or more detectors, and the one or more motion signals generated by the one or more inertial sensors.

In an example embodiment, a non-transitory computer-readable medium which stores instructions that are executable by one or more processors of a wearable computing device is provided. The non-transitory computer-readable medium stores instructions which includes instructions to cause the one or more processors to receive information indicating an amount of ambient light in a surrounding environment of the wearable computing device detected by a first sensor disposed at an upper part of a body of the wearable computing device, and instructions to cause the one or more processors to adjust a current supplied to one or more light sources of a second sensor based on the amount of ambient light detected by the first sensor. The second sensor is disposed at a lower part of the body and includes the one or more light sources which emit light toward a body part of a user when the wearable computing device is worn by the user and one or more detectors which receive a reflection of the light emitted toward the body part to generate a signal indicating a biometric of the user.

In an embodiment, the non-transitory computer-readable medium stores instructions which includes instructions to cause the one or more processors to receive information indicating a type of motion of the wearable computing device and/or an amplitude of movement of the wearable computing device, based on one or more motion signals generated by one or more inertial sensors disposed in the body of the wearable computing device. In an embodiment, the non-transitory computer-readable medium stores instructions which includes instructions to cause the one or more processors to adjust the current supplied to the one or more light sources based on the information indicating the type of motion of the wearable computing device and/or the amplitude of movement of the wearable computing device. The non-transitory computer-readable medium may store additional instructions to execute other aspects of the wearable computing device and computer-implemented method as described herein.

These and other features, aspects, and advantages of various embodiments of the disclosure will become better understood with reference to the following description, drawings, and appended claims. The accompanying drawings, which are incorporated in and constitute a part of this specification, illustrate example embodiments of the disclosure and, together with the description, serve to explain the related principles.

BRIEF DESCRIPTION OF THE DRAWINGS

Detailed discussion of example embodiments directed to one of ordinary skill in the art is set forth in the specification, which makes reference to the appended drawings, in which.

DETAILED DESCRIPTION

Figure 1:
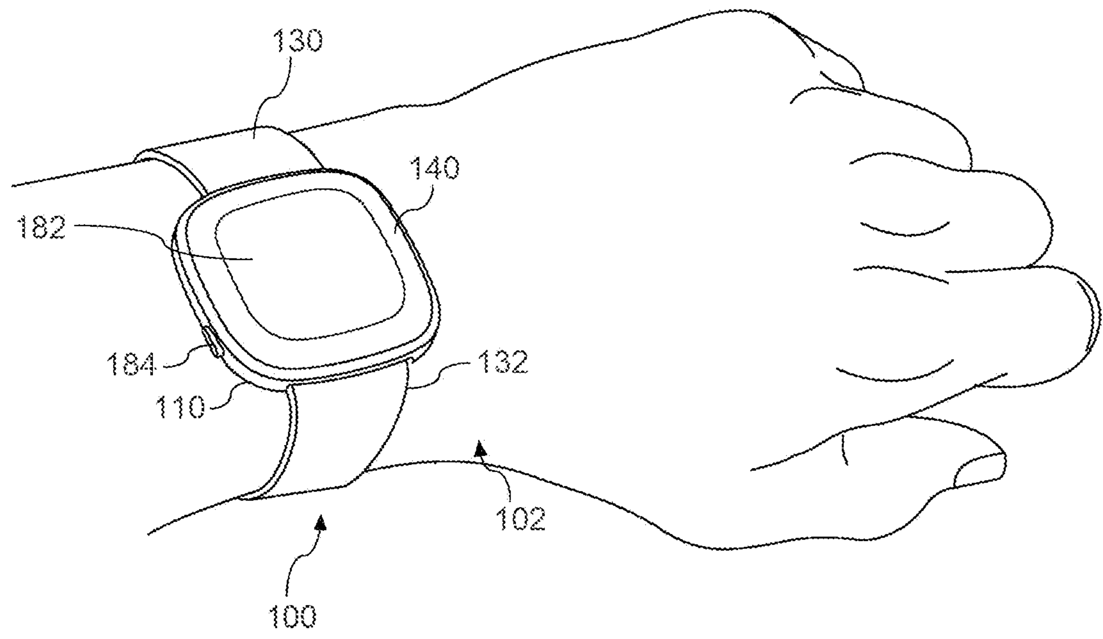
FIG. 1 depicts an example wearable computing device according to according to one or more example embodiments of the disclosure.

Reference now will be made to embodiments of the disclosure, one or more examples of which are illustrated in the drawings. Each example is provided by way of explanation of the disclosure and is not intended to limit the disclosure. In fact, it will be apparent to those skilled in the art that various modifications and variations can be made to disclosure without departing from the scope or spirit of the disclosure. For instance, features illustrated or described as part of one embodiment can be used with another embodiment to yield a still further embodiment. Thus, it is intended that the disclosure covers such modifications and variations as come within the scope of the appended claims and their equivalents.

Terms used herein are used to describe the example embodiments and are not intended to limit and/or restrict the disclosure. The singular forms "a," "an" and "the" are intended to include the plural forms as well, unless the context clearly indicates otherwise. In this disclosure, terms such as "including", "having", "comprising", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, the elements are not limited by these terms. Instead, these terms are used to distinguish one element from another element. For example, without departing from the scope of the disclosure, a first element may be termed as a second element, and a second element may be termed as a first element.

The term "and/or" includes a combination of a plurality of related listed items or any item of the plurality of related listed items. For example, the scope of the expression or phrase "A and/or B" includes the item "A", the item "B", and the combination of items "A and B".

In addition, the scope of the expression or phrase "at least one of A or B" is intended to include all of the following: (1) at least one of A, (2) at least one of B, and (3) at least one of A and at least one of B. Likewise, the scope of the expression or phrase "at least one of A, B, or C" is intended to include all of the following: (1) at least one of A, (2) at least one of B, (3) at least one of C, (4) at least one of A and at least one of B, (5) at least one of A and at least one of C, (6) at least one of B and at least one of C, and (7) at least one of A, at least one of B, and at least one of C.

Examples of the disclosure are directed to a wearable computing device that can be worn, for example, on a user's wrist. For example, the wearable computing device may include a watch or a fitness device. The wearable computing device includes a body with a first sensor (e.g., an ambient light sensor) disposed at an upper part of the body. The first sensor is configured to detect ambient light in a surrounding environment of the wearable computing device. The wearable computing device includes a second sensor (e.g., a PPG sensor) disposed at a lower part of the body. The second sensor is configured to generate a signal indicating a biological attribute (e.g., heart rate or pulse information) of the user. The second sensor includes one or more light sources (e.g., light emitting diodes (LEDs)) configured to emit light toward a body part of the user when the wearable computing device is worn by the user and one or more detectors (e.g., photodiodes) configured to receive a reflection of the light emitted toward the body part to generate the signal indicating the biological attribute of the user. The wearable computing device includes one or more processors configured to adjust a current supplied to the one or more light sources based on an amount of ambient light detected by the first sensor. For example, based on the amount of ambient light detected by the first sensor, the one or more processors may increase a current supplied to the one or more light sources (e.g., in a bright ambient environment) to improve a measurement accuracy of the second sensor, or may decrease a current supplied to the one or more light sources (e.g., in a dim ambient environment) to extend a battery life of the wearable computing device.

In an embodiment the wearable computing device may also include one or more inertial sensors configured to generate one or more motion signals based on a movement of the wearable computing device, wherein the one or more processors are configured to adjust the current supplied to the one or more light sources based on the one or more motion signals generated by the one or more inertial sensors. The one or more inertial sensors may include an accelerometer and/or gyroscope, for example. The one or more processors may be configured to adjust a current supplied to the one or more light sources based on whether the one or more motion signals generated by the inertial sensors indicates a movement of the wearable computing device is greater than a threshold level (i.e., a degree, or rate of movement likely to cause the detectors of the PPG sensor to be exposed to ambient light, such as 2 m/s) and/or indicates a type of movement of the wearable computing device that may affect an accuracy of the PPG sensor (e.g., a tilting of the wearable computing device that may be likely to cause the detectors of the PPG sensor to be exposed to ambient light, a pattern of movement of the wearable computing device which infers a user is engaging in exercise or running). For example, based on the amount and/or type of movement indicated by the one or more motion signals generated by the inertial sensors, the one or more processors may increase a current supplied to the one or more light sources (e.g., an amount of movement of the wearable computing device being greater than a threshold value) to improve a measurement accuracy of the second sensor, or may decrease a current supplied to the one or more light sources (e.g., when the wearable computing device is stationary) to extend a battery life of the wearable computing device.

Photoplethysmography (PPG) is an optical technique to obtain blood volume change data. PPG sensors may optically measure biometric information such as a heart rate, using a emitter (light source) and a detector (e.g., a photodiode) at the surface of a user's body part to measure the volumetric variations of blood circulation. The light source (e.g., one or more LEDs) emits light to a body part and the photodetector measures the reflected light from the body part, where the amount of reflected light may indicate biometric information about the user (e.g., blood flow, volume of blood, etc.). The light source may emit infrared light, and the color of the LED may be red, green, or yellow. The PPG signal may include various components, such as a DC component (or DC offset), which represents the constant absorption of light passing through the tissues, an AC component generated by heartbeats (cardiac activity) affecting blood volume, which depends on the systolic and diastolic phases, and an ambient light component which represents an amount of ambient light received by the detector (e.g., photodiode).

The quality of the PPG signal affects the accuracy of a measured heartrate. The quality of the PPG signal may be dependent on, among other things, optical sensor design and parameters, such as the window and lens design and spacing of the PPG detectors (e.g., photodiodes) and light sources (e.g., LEDs). The optical sensor design and parameters also include a brightness level of the light source(s) (e.g., LED (s)), a number of detectors (e.g., photodiodes) implemented, and a location of the light source(s) and detectors. The optical sensor design and parameters also include a number of optical paths.

PPG sensors of wearable computing devices may be vulnerable to light leakage by which detectors of the PPG sensor are exposed to ambient light from the environment, thus negatively affecting the accuracy of the PPG signal. For example, in bright ambient environments, it is possible for high motion activities to cause the wearable computing device to move or "bob" on a user's body part (e.g., their wrist), resulting in a gap between the user's body part and a bottom of the wearable computing device where the PPG sensor is located. Light can leak into the gap and be exposed to the detectors of the PPG sensor and/or interfere with the light emitted by the light source to the body part, thereby corrupting the PPG signal that is obtained by the detectors.

According to one or more examples disclosed herein, corruption of the PPG signal due to ambient light may be compensated for, mitigated, or overcome by increasing the brightness of the light source(s) (LED(s)) opportunistically or selectively. For example, the brightness of the light source(s) may be selectively increased based on an ambient environment light and/or user activity (e.g., motion of a user). For example, adjusting a brightness of the light source (e.g., by adjusting a current) may be performed only while the user is exercising (i.e., when a movement of the wearable computing device exceeds a threshold level), or may be performed at all points during the day. For example, the one or more processors may be configured to keep the light source brightness low when brighter light is not needed, thus saving power. When brighter light is needed to increase an accuracy of the PPG signal, such as in a bright environment and/or during a high motion activity, the one or more processors may be configured to increase a supply of current to the light source to increase the brightness of the light source while consuming more power for a shorter amount of time (e.g., compared to a wearable computing device which continuously operates the light source at a high level of brightness).

According to one or more examples of the disclosure, operations of the wearable computing device include one or more of the first sensor (e.g., ambient light sensor), second sensor (e.g., PPG sensor detectors), and inertial sensors (e.g., accelerometer and/or gyroscope), providing information (e.g., signals, data, etc.) as an input to the one or more processors which determine whether a current supplied to the light source (e.g., LED) of the PPG sensor should be adjusted.

For example, the ambient light sensor may provide a raw signal to an ambient environment brightness determination unit (e.g., an analog-digital converter) which converts the raw signal into a value representing an ambient light magnitude (e.g., a lux value). For example, the ambient environment brightness determination unit may be implemented as part of the ambient light sensor firmware, or may be separately from the ambient light sensor as an internal unit to the wearable computing device. The post-processed value representing the ambient light magnitude (e.g., a value in lux, rather than a raw signal) may be transmitted to the one or more processors for determining whether a current supplied to the light source (e.g., LED) of the PPG sensor should be adjusted.

For example, the inertial sensors (e.g., an inertial measurement unit) may constantly measure motion data of the wearable computing device. The motion data may be transmitted to the one or more processors. For example, the motion data may be transmitted to the one or more processors after being passed through a coarse classifier model in order to understand or classify certain characteristics regarding the motion of the wearable computing device (e.g., if the motion is considered low, medium, high, periodic, aperiodic, etc.).

For example, the one or more detectors of the PPG sensor may also sense ambient light when a bottom side of the wearable computing device is tilted or separated from the body part of the user. The detectors of the PPG sensor may provide information (e.g., via a raw signal) relating to an ambient light condition to an ambient environment brightness determination unit (e.g., an analog-digital converter) which converts one or more raw signals from the detectors of the PPG sensor into a value representing an ambient light magnitude (e.g., a lux value). For example, the ambient environment brightness determination unit may receive the one or more raw signals from the one or more detectors of the PPG sensor as well as receive the raw signal from the ambient light sensor or may receive only the one or more raw signals from the one or more detectors of the PPG sensor when an ambient environment brightness determination unit is implemented as part of the ambient light sensor firmware. In another example, a separate ambient environment brightness determination unit may be provided to receive the raw signal from the ambient light sensor and the one or more raw signals from the one or more detectors of the PPG sensor. The post-processed value representing the ambient light magnitude (e.g., a value in lux, rather than a raw signal) sensed by the one or more detectors of the PPG sensor may be transmitted to the one or more processors for determining whether a current supplied to the light source (e.g., LED) of the PPG sensor should be adjusted. For example, the one or more detectors may be configured to detect ambient light in a space between the lower part of the body of the wearable computing device and the body part of the user and the one or more processors may be configured to adjust the current supplied to the one or more light sources based on an amount of ambient light detected by the one or more detectors.

The wearable computing device may include one or more memories to store settings of the light source, including a current setting of the light source, which acts as a reference point. For example, the PPG analog front end (AFE) may have awareness of a current LED brightness setting (e.g., a current level currently supplied to the LED) and provide the current LED brightness setting to the one or more processors for determining whether a current supplied to the light source (e.g., LED) of the PPG sensor should be adjusted. The one or more processors may use one or more of the inputs from the ambient light sensor, inertial sensors, and detectors, as well as the current LED brightness setting, to determine whether a current supplied to the light source (e.g., LED) of the PPG sensor should be adjusted. When the one or more processors determine a brightness value needed for the LED to generate an accurate PPG signal is satisfied based on the current LED brightness setting, no adjustment may be made. Conversely, when the one or more processors determine a brightness value needed for the LED to generate an accurate PPG signal can be satisfied by adjusting (e.g., lowering or increasing) the current LED brightness setting, the one or more processors may control a LED driver to adjust an amount of current supplied to the LED, accordingly. After an updated brightness value is determined by the one or more processors, the one or more processors may feed the updated brightness value back to the AFE to adjust the brightness (i.e., the current) to the updated brightness value. For example, the one or more processors may control an LED driver to increase or decrease a current supplied to the LED. For example, the LED may be driven at various current levels based on one or more of the inputs from the ambient light sensor, inertial sensors, and detectors.

The LED brightness setting value (i.e., an amount of current to be supplied to the LED), may be obtained or determined by the one or more processors: (1) based on a lookup table derived from laboratory evaluations of optimal parameters, where ambient light values and motion data are the primary inputs; (2) based on a linear scaling (e.g., [motion+more ambient light]*scaling factor=new brightness value); and/or (3) based on a nonlinear scaling, developed by training a machine learning model that leverages ambient light values and motion data as inputs and outputs an optimal LED brightness setting value (i.e., an amount of current to be supplied to the LED) given the environmental conditions. For example, the one or more processors may control the LED driver to increase an amount of current supplied to the LED to increase a brightness of the LED where the ambient light sensor detects a brighter environment and/or where the inertial sensors detect high movement of the wearable computing device.

For example, the LED may be driven at a low setting (e.g., about 50 mA), a medium setting (e.g., about 100 mA), a high setting (e.g., about 200 mA), and a very high setting (e.g., about 250 mA). A low setting may be appropriate where a user is stationary and an amount of ambient light detected is low, a medium setting may be appropriate where a user is stationary and an amount of ambient light detected is medium, a high setting may be appropriate where a user is moderately active and/or an amount of ambient light detected is high, and a very high setting may be appropriate where a user is very active and/or an amount of ambient light detected is very high. However, the disclosure is not limited to these examples and other conditions may warrant different settings for the LED. In addition, the disclosure is not limited to the example LED current values and other values, e.g., intermediate values may be used, for example, as determined using a machine learning model.

The first sensor can include, for example, an ambient light sensor (ALS) disposed at an upper part of a body of the wearable computing device and below a display which is also disposed at the upper part of the body and which is configured to display biometric information. The ALS may output information indicative of ambient light in the surrounding environment of the wearable computing device. The one or more processors may receive the information indicative of the ambient light in the surrounding environment of the wearable computing device and control a brightness level of the display based on the information received from the ALS. For example, the ambient light sensor may have a first sampling rate (e.g., detecting an amount of ambient light about every 200 ms) to detect the ambient light in a first operating mode (e.g., an interactive mode) of the wearable computing device, and a second sampling rate (e.g., detecting an amount of ambient light about every 1 second) to detect the ambient light in a second operating mode (e.g., an always-on display mode) of the wearable computing device.

The second sensor can include, for example, one or more multipath photoplethysmography (PPG) sensors which can be used to monitor a heart rate of the user when the wearable computing device is worn by the user. The one or more PPG sensors may include one or more light sources or emitters (e.g., light-emitting diodes (LEDs)) and one or more detectors (e.g., photodiodes). In an example configuration, the one or more PPG sensors may be disposed at a lower part of the body of the wearable computing device to face toward a body part of the user when the wearable computing device is worn by the user. For example, the one or more PPG sensors may be in contact with the body part of the user when the wearable computing device is worn by the user so that an accuracy of the one or more PPG signals output by the one or more PPG sensors is increased.

In an example configuration, the one or more PPG sensors may include a single LED disposed in a central portion of a bottom of the wearable computing device, and a plurality of detectors (e.g., four detectors) disposed around the LED in a circumferential manner, with each of the four detectors being spaced apart from one another along the circumferential direction. In another example configuration, the one or more PPG sensors may include a single LED and three detectors. The LED may be disposed on a first side of the bottom of the wearable computing device, opposite to a second detector which is disposed on a second side of the bottom of the wearable computing device. A first detector may be disposed on a third side of the bottom of the wearable computing device, opposite to a third detector which is disposed on a fourth side of the bottom of the wearable computing device. The LED and second detector may be disposed between the first and third detectors in a first (x) direction, and the first and third detectors may be disposed between the LED and second detector in a second (y) direction. As another example, the one or more PPG sensors may include a plurality of LEDs and a plurality of detectors. The plurality of LEDs may be disposed in a central portion of the bottom of the wearable computing device and the plurality of detectors disposed outward of the LEDs.

According to one or more examples of the disclosure, when the PPG sensor includes a plurality of LEDs and one or more motion signals generated by the one or more inertial sensors indicate at least part of a bottom side of the wearable computing device is spaced apart from a body part of the user (e.g., by a predetermined amount or by a predetermined angle), the one or more processors may be configured to cut off current supplied to the at least one of the LEDs (e.g., those LEDs which are located on a side of the wearable computing device that is most spaced apart from the body part of the user), and to increase current supplied to one or more remaining LEDs (e.g., those LEDs which are located on a side of the wearable computing device which remains in contact with the body part of the user or is closest to the body part of the user). For example, the one or more processors may determine at least part of a bottom side of the wearable computing device is not in contact with the body part of the user based on a tilt angle of the wearable computing device detected by the inertial sensors and/or based on a movement of the wearable computing device.

Example aspects of the disclosure are also directed to computer implemented methods of a wearable computing device. The method may include detecting, by a first sensor disposed at an upper part of a body of a wearable computing device, ambient light in a surrounding environment of the wearable computing device, and adjusting, by one or more processors, a current supplied to one or more light sources of a second sensor based on an amount of ambient light detected by the first sensor. The second sensor may be disposed at a lower part of the body and include the one or more light sources which emit light toward a body part of a user when the wearable computing device is worn by the user and one or more detectors which receive a reflection of the light emitted toward the body part to generate a signal indicating a biological attribute of the user.

The method may further include generating, by one or more inertial sensors disposed in the body, one or more motion signals based on a movement of the wearable computing device, and adjusting, by the one or more processors, the current supplied to the one or more light sources of the second sensor, based on the one or more motion signals generated by the one or more inertial sensors. In response to the one or more motion signals generated by the one or more inertial sensors indicating a motion of the wearable computing device is of a predetermined type or is greater than a threshold value, the method may include increasing the current supplied to the one or more light sources. For example, the method may include increasing the current supplied to the one or more light sources to a peak value when the amount of ambient light detected by the first sensor is greater than a first threshold value and the one or more motion signals generated by the one or more inertial sensors indicate a motion of the wearable computing device is of a predetermined type or is greater than a second threshold value. The peak value may correspond to a maximum current setting for the light source (e.g., LED).

The second sensor may be a PPG sensor having a plurality of light-emitting diodes (LEDs). In response to the one or more motion signals generated by the one or more inertial sensors indicating at least one of the LEDs is spaced apart from a body part of the user, the method may further include cutting off current supplied to the at least one of the LEDs, and increasing current supplied to one or more remaining LEDs of the plurality of LEDs which are in contact with the body part of the user.

The method may further include displaying, on a display of the wearable computing device, biometric information, where the first sensor is an ambient light sensor disposed below the display. The method may include detecting the ambient light by the first sensor by sampling the ambient light at a first sampling rate in a first operating mode of the wearable computing device, and at a second sampling rate in a second operating mode of the wearable computing device. The first operating mode may be an interactive mode and the second operating mode may be an always-on display mode. The first sampling rate (e.g., detecting an amount of ambient light about every 200 ms) may be more frequent than the second sampling rate (e.g., detecting an amount of ambient light about every 1 second).

The method may further include detecting, by the one or more detectors, ambient light in a space between the lower part of the body and the body part of the user, and adjusting, by the one or more processors, the current supplied to the one or more light sources of the second sensor, based on an amount of ambient light detected by the one or more detectors.

The method may further include determining, by the one or more processors, a current value for which the current is to be adjusted to, according to one or more of a lookup table, a linear scaling method, and a nonlinear scaling method, using one or more of an amount of ambient light detected by the first sensor, an amount of ambient light detected by the one or more detectors, and one or more motion signals generated by one or more inertial sensors based on a movement of the wearable computing device, as input(s).

The method may further include any of the other operations of the wearable computing device as described herein.

Example aspects of the disclosure are also directed to a non-transitory computer-readable medium which stores instructions that are executable by one or more processors of a wearable computing device. For example, the instructions may include instructions to cause the one or more processors to receive information indicating an amount of ambient light in a surrounding environment of the wearable computing device detected by a first sensor disposed at an upper part of a body of a wearable computing device. The instructions may further include instructions to cause the one or more processors to adjust a current supplied to one or more light sources of a second sensor based on the amount of ambient light detected by the first sensor. The second sensor may be disposed at a lower part of the body and include the one or more light sources which emit light toward a body part of a user when the wearable computing device is worn by the user and one or more detectors which receive a reflection of the light emitted toward the body part to generate a signal indicating a biological attribute of the user.

The instructions may further include instructions to cause the one or more processors to receive information indicating a type of motion of the wearable computing device and/or an amplitude of movement of the wearable computing device, based on one or more motion signals generated by one or more inertial sensors disposed in the body of the wearable computing device. The instructions to cause the one or more processors to adjust the current supplied to the one or more light sources may be further based on the information indicating the type of motion of the wearable computing device and/or the amplitude of movement of the wearable computing device.

The non-transitory computer-readable medium may further store instructions which include instructions to cause the one or more processors to carry out any of the operations of the wearable computing device and method as described herein.

Example aspects of the disclosure provide several technical effects, benefits, and/or improvements in computing technology and the technology of wearable computing devices. For example, according to one or more examples of the disclosure, battery life of the wearable computing device may be extended by adjusting a current supplied to a light source based on an ambient light sensed by the wearable computing device and/or a motion of the wearable computing device. For example, power consumed by the wearable computing device may be conserved by operating the light source at a lower power level when an amount of sensed ambient light is low (e.g., less than a threshold level). For example, power consumed by the wearable computing device may be conserved by operating the light source at a lower power level when an amount of sensed movement is low or a type of movement of the wearable computing device is not likely to cause an accuracy of the PPG sensor to be degraded (e.g., not likely to be degraded beyond a threshold amount).

For example, according to one or more examples of the disclosure, a measurement accuracy of a PPG sensor of the wearable computing device may be increased (or maintained or prevented from decreasing) by adjusting a current supplied to a light source based on an ambient light sensed by the wearable computing device and/or a motion of the wearable computing device. For example, the measurement accuracy of the PPG sensor of the wearable computing device may be increased (or maintained or prevented from decreasing) by operating the light source at a higher power level when an amount of sensed ambient light is high (e.g., greater than a threshold level). For example, the measurement accuracy of the PPG sensor of the wearable computing device may be increased (or maintained or prevented from decreasing) by operating the light source at a higher power level when an amount of sensed movement is high or a type of movement of the wearable computing device is likely to cause an accuracy of the PPG sensor to be degraded (e.g., to be degraded beyond a threshold amount).

Furthermore, according to one or more examples of the disclosure the wearable computing device leverages sensors which may be pre-existing in the wearable computing device. For example, the pre-existing sensors may include ambient light sensors used for other purposes, such as detecting ambient light to change a brightness level of the display screen according to environmental conditions, but which can also be used to detect an amount of ambient light which is present that may affect an accuracy of the PPG sensor. Therefore, it is not necessary to add further sensors to the wearable computing device to adjust a current level of a light source (e.g., an LED) for a PPG sensor. For example, the pre-existing sensors may include inertial sensors (e.g., an accelerometer and/or gyroscope) used for other purposes, such as detecting a motion of the wearable computing device to count steps of the user or measure other activities of the user, but which can also be used to determine that an accuracy of the PPG sensor may be degraded due to the movement of the wearable computing device. Therefore, it is not necessary to add further sensors to the wearable computing device to adjust a current level of a light source (e.g., an LED) for a PPG sensor. As another example, the pre-existing sensors may also include detectors of the PPG sensor which are used to receive a reflection of the light emitted toward a body part of a user, but which can also be used to detect an amount of ambient light which is present that may affect an accuracy of the PPG sensor. Therefore, it is not necessary to add further sensors to the wearable computing device to adjust a current level of a light source (e.g., an LED) for a PPG sensor based on an amount of ambient light detected.

Figure 2:
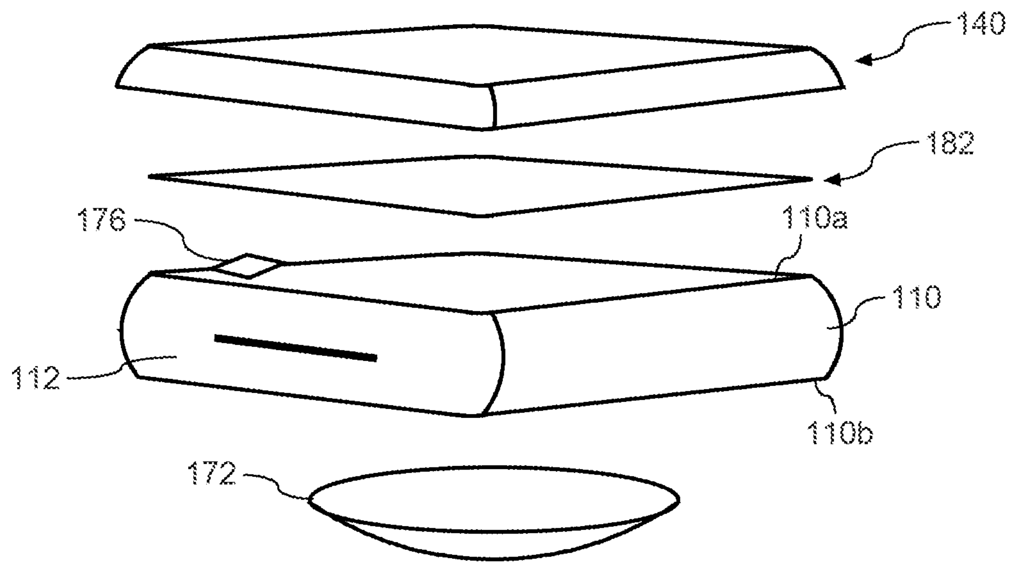
FIG. 2 depicts an exploded view of an example wearable computing device according to one or more example embodiments of the disclosure.

Referring now to the drawings, FIGS. 1 through 6 illustrate examples of a wearable computing device 100 according to various examples of the disclosure. FIG. 1 illustrates an example wearable computing device 100 which can be worn, for example, on a body part 102 (e.g., an arm, wrist, etc.) of a user. In FIG. 1, the wearable computing device 100 includes a body 110. FIG. 2 illustrates an exploded view of the wearable computing device 100 where the body 110 includes an upper part 110*a* and a lower part 110*b*, and the body 110 defines a cavity 112 in which one or more electronic components (e.g., disposed on one or more printed circuit boards) are disposed. In the example of FIG. 1, the wearable computing device 100 includes a printed circuit board disposed within the cavity 112. Furthermore, one or more electronic components are disposed on the printed circuit board. The wearable computing device 100 can further include a battery that is disposed within the cavity 112 defined by the body 110. The wearable computing device 100 further includes various sensors 170 that are disposed within the cavity 112 defined by the body 110. For example, the sensors 170 may include multipath photoplethysmography (PPG) sensors 172 disposed at the lower side 110*b* of the body 110 which may be used to monitor a heart rate of the user. The PPG sensors 172 include one or more emitters (e.g., light-emitting diodes (LEDs)) and a plurality of detectors (e.g., photodiodes). Light emitted from the one or more emitters is transmitted in a direction toward the user's body part (e.g., a portion of a user's wrist) which is in contact with the lower side 110*b* of the body 110. The light then interacts with blood vessels of the user, where it is modified to a degree that is influenced by the current blood volume in the blood vessels. The modified light is directed back toward the PPG detectors by reflection and/or refraction. The PPG detectors generate data (e.g., one or more signals) which is reflective of the current blood volume of the blood vessels of the user which received the light emitted from the one or more emitters. For example, the sensors 170 may also include inertial sensors 174 which may include an accelerometer 174*a* and/or a gyroscope 174*b*, as well as other sensors such as a magnetometer. The accelerometer 174*a* may be used to capture motion information with respect to the wearable computing device 100. The gyroscope 174*b* may also be used additionally or alternatively to capture motion information with respect to the wearable computing device 100. Other sensors such as a magnetometer, GPS sensor, and the like may also be included in the wearable computing device 100.

In FIG. 1 the wearable computing device 100 includes a first band 130 and a second band 132. As shown, the first band 130 is coupled to the body 110 at a first location thereon. Conversely, the second band 132 is coupled to the body 110 at a second location thereon. Furthermore, the first band 130 and the second band 132 can be coupled to one another to secure the body 110 to the body part 102 of the user.

In some examples, the first band 130 can include a buckle or clasp (not shown). Additionally, the second band 132 can include a plurality of apertures (not shown) spaced apart from one another along a length of the second band 132. In such implementations, a prong of the buckle associated with the first band 130 can extend through one of the plurality of openings defined by the second band 132 to couple the first band 130 to the second band 132. It should be appreciated that the first band 130 can be coupled to the second band 132 using any suitable type of fastener. For example, in an embodiment, the first band 130 and the second band 132 can include a magnet. In such implementations, the first band 130 and the second band 132 can be magnetically coupled to one another to secure the body 110 to a body part 102 (e.g., an arm) of the user.

In FIG. 1, the wearable computing device 100 includes a cover 140 positioned on the body 110 so that the cover 140 is positioned on top of a display 182. In this manner, the cover 140 can protect the display 182 from being scratched. In an embodiment, the wearable computing device 100 can include a seal (not shown) positioned between the body 110 and the cover 140. For instance, a first surface of the seal can contact the body 110 and a second surface of the seal can contact the cover 140. In this manner, the seal between the body 110 and the cover 140 can prevent a liquid (e.g., water) from entering the cavity 112 defined by the body 110.

It should be understood that the cover 140 can be optically transparent so that the user can view information being displayed on the display 182. For instance, in an embodiment, the cover 140 can include a glass material. It should be understood, however, that the cover 140 can include any suitable optically transparent material.

In FIG. 1, the wearable computing device 100 includes an ambient light sensor (ALS) 176 positioned at an upper part of the body 110 beneath the display 182 and the cover 140. The ALS 176 is configured to detect ambient light in a surrounding environment of the wearable computing device 100. For example, the ALS 176 may detect ambient light through the cover 140, which may be transparent. For example, the ALS 176 may be disposed at a peripheral region of the body 110. For example, the ALS 176 may have a first sampling rate (e.g., detecting an amount of ambient light about every 200 ms) to detect the ambient light when the wearable computing device 100 is operated in a first operating mode (e.g., an interactive mode), and a second sampling rate (e.g., detecting an amount of ambient light about every 1 second) to detect the ambient light when the wearable computing device 100 is operated in a second operating mode (e.g., an always-on display mode).

Figure 3:
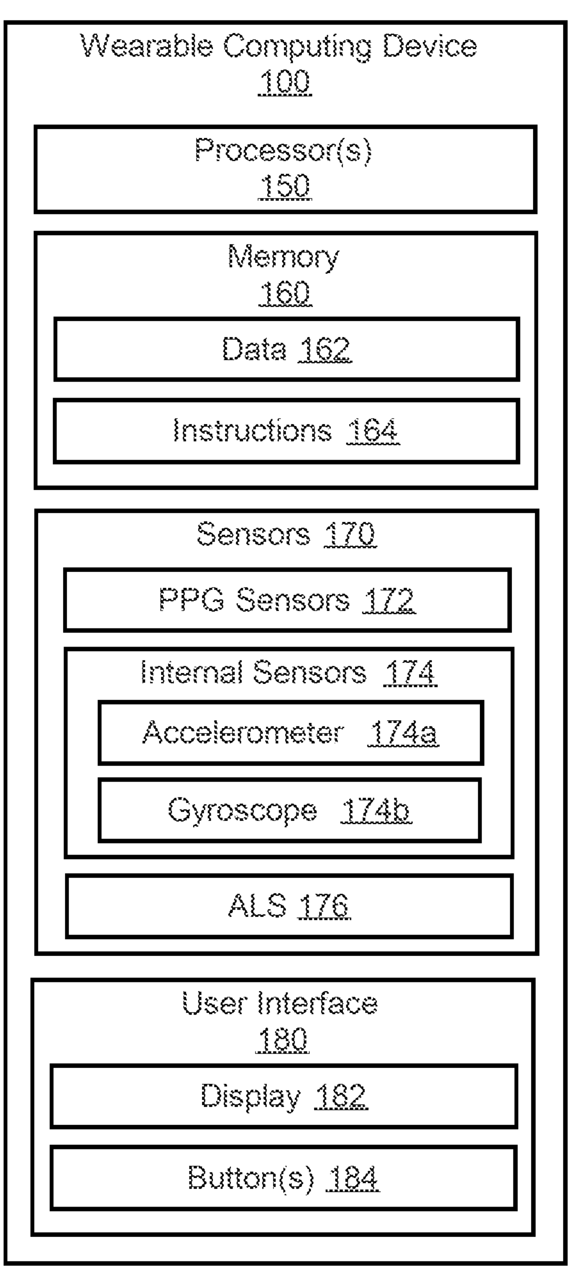
FIG. 3 depicts an example block diagram of the wearable computing device according to one or more example embodiments of the disclosure.

The one or more processors 150, which are included in the wearable computing device 100 as shown in FIG. 3, receive information indicative of the ambient light in the surrounding environment of the wearable computing device 100 and control a brightness level of the display 182 based on the information received from the ALS 176. For example, the output of the ALS 176 may be used for both controlling a brightness level of the display 182 as well as controlling an amount of current supplied to a light source of the PPG sensor 172. Therefore, usage (e.g., a duty cycle) of the ALS 176 is not increased for purposes of adjusting the current supplied to the light source of the PPG sensor 172, as the one or more processors 150 may use the same output from the ALS 176 for controlling a brightness of the display 182 as for adjusting the current supplied to the light source of the PPG sensor 172.

FIG. 3 illustrates an example block diagram of the wearable computing device 100 according to one or more example embodiments of the disclosure. In FIG. 3, the wearable computing device 100 includes one or more processors 150, one or more memory devices 160, one or more sensors 170, and a user interface 180.

For example, the one or more processors 150 can be any suitable processing device that can be included in a wearable computing device 100. For example, such a processor 150 may include one or more of a processor, processor cores, a controller and an arithmetic logic unit, a central processing unit (CPU), a graphics processing unit (GPU), a digital signal processor (DSP), an image processor, a microcomputer, a field programmable array, a programmable logic unit, an application-specific integrated circuit (ASIC), a microprocessor, a microcontroller, etc., and combinations thereof, including any other device capable of responding to and executing instructions in a defined manner. The one or more processors 150 can be a single processor or a plurality of processors that are operatively connected, for example in parallel.

The memory 160 can include one or more non-transitory computer-readable storage mediums, such as such as a Read Only Memory (ROM), Programmable Read Only Memory (PROM), Erasable Programmable Read Only Memory (EPROM), and flash memory, a USB drive, a volatile memory device such as a Random Access Memory (RAM), a hard disk, floppy disks, a blue-ray disk, or optical media such as CD ROM discs and DVDs, and combinations thereof. However, examples of the memory 160 are not limited to the above description, and the memory 160 may be realized by other various devices and structures as would be understood by those skilled in the art.

For example, memory 160 can store instructions, that when executed, cause the one or more processors 150 to adjust a current supplied to one or more light sources of the PPG sensor 172, based on one or more of an amount of ambient light sensed by the ALS 176, an amount of ambient light sensed by one or more detectors of the PPG sensor 172, and an amplitude and/or a type of motion of the wearable computing device 100 sensed by the inertial sensors 174, as described according to examples of the disclosure.

Memory 160 can also include data 162 and instructions 164 that can be retrieved, manipulated, created, or stored by the one or more processor(s) 150. In some example embodiments, such data can be accessed and used as input to adjust a current supplied to one or more light sources of the PPG sensor 172, based on one or more of an amount of ambient light sensed by the ALS 176, an amount of ambient light sensed by one or more detectors of the PPG sensor 172, and an amplitude and/or a type of motion of the wearable computing device 100 sensed by the inertial sensors 174, as described according to examples of the disclosure.

In FIG. 3, the wearable computing device 100 includes a user interface 180 configured to receive an input from a user (e.g., via a touch input such as a thumb, finger, or an input device such as a stylus or pen). The wearable computing device 100 may execute a function in response to receiving the input from the user (e.g., checking health information about the user such as a blood pressure, making and/or receiving a phone call, sending and/or receiving a text message, obtaining a current time, setting a timer, a stop-watch function, controlling an external device such as a home appliance, and the like).

In FIG. 3, the user interface 180 includes the display 182 which displays information viewable by the user (e.g., time, date, biometric information, notifications, etc.). For example, the display 182 may be a non-touch sensitive display or a touch-sensitive display. The display 182 may include a liquid crystal display (LCD), a light emitting diode (LED) display, an organic light emitting diode (OLED) display, active matrix organic light emitting diode (AMO-LED), flexible display, 3D display, a plasma display panel (PDP), a cathode ray tube (CRT) display, and the like, for example. However, the disclosure is not limited to these example displays and may include other types of displays. The display 182 may have a square or rectangular shape, or may be annular in shape (e.g., elliptical, circular, etc.). However, the shape of the display 182 is not limited thereto.

The user interface 180 may additionally, or alternatively, include one or more buttons 184 to receive an input from a user by the user applying a force to the button 184. The button 184 may be included on one or more peripheral sides of the wearable computing device 100 as shown in FIG. 1, for example. The button 184 may include mechanical components and/or electrical circuitry to implement a function of the wearable computing device 100 (e.g., setting a time, changing a setting and/or view of the display 182, selecting an option displayed on the display 182).

Figure 4:
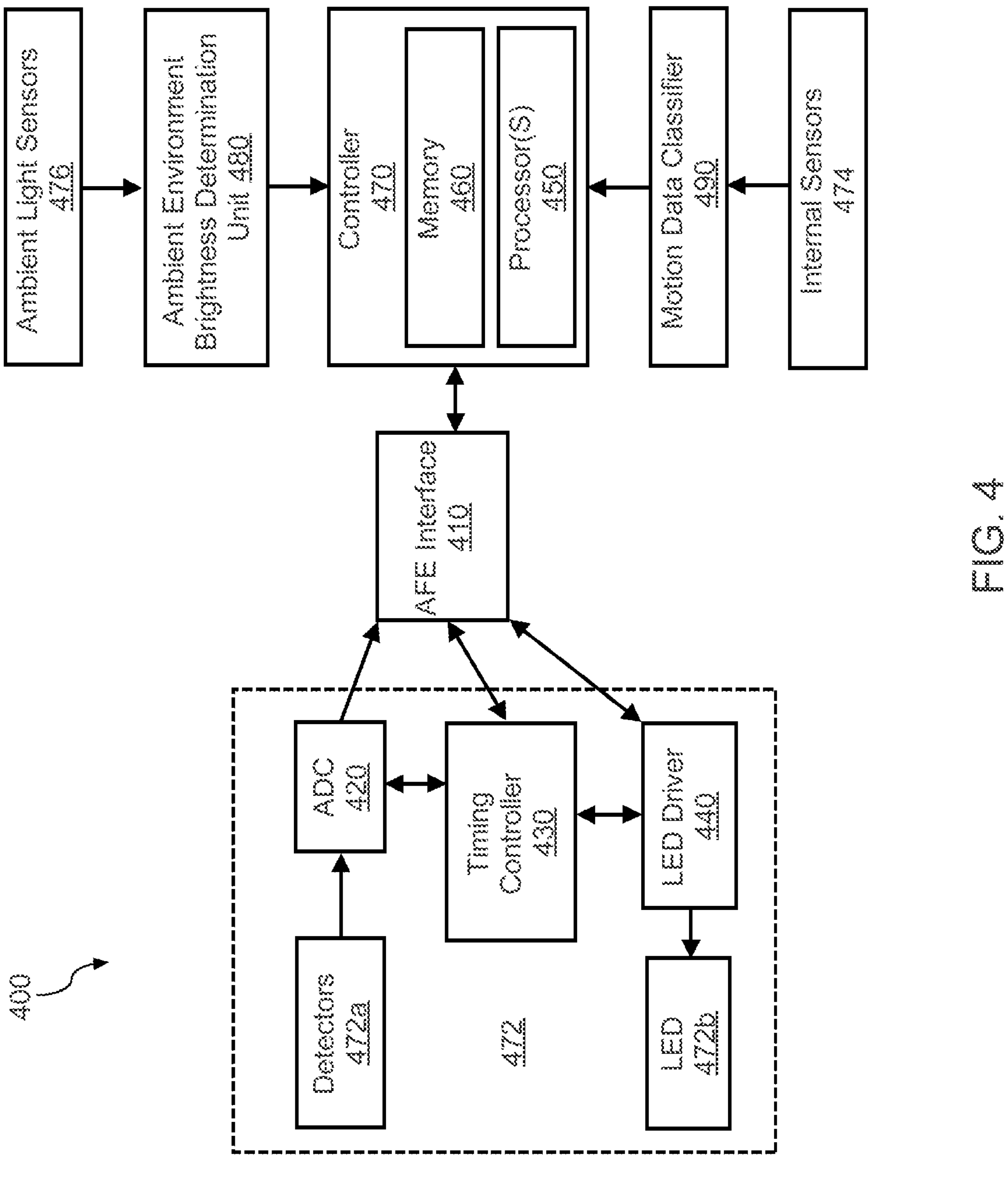
FIG. 4 depicts an example block diagram of the wearable computing device according to one or more example embodiments of the disclosure.

FIG. 4 illustrates an example block diagram of the wearable computing device 400 according to one or more example embodiments of the disclosure. In FIG. 4, the wearable computing device 400 includes a controller 470 which includes one or more processors 450 and one or more memory devices 460. The one or more processors 450 and one or more memory devices 460 may correspond to the one or more processors 150 and one or more memory devices 160 described previously. The wearable computing device 400 includes a PPG sensor 472, inertial sensors 474 (optional), and ambient light sensor 476. The PPG sensor 472, inertial sensors 474, and ambient light sensor 476 may correspond to the PPG sensor 172, inertial sensors 174, and ambient light sensor 176 described previously. Other components of the wearable computing device 100 not shown in FIG. 4 (e.g., the user interface 180, display 182, and button (s) 184) may be included in the wearable computing device 400, but are not shown for ease of explanation.

The ambient light sensor 476 may provide a raw signal to an ambient environment brightness determination unit 480 (e.g., an analog-digital converter) which is configured to convert the raw signal into a value representing an ambient light magnitude (e.g., a lux value). For example, the ambient environment brightness determination unit 480 may be integrated with the ambient light sensor 476 and implemented as part of the ambient light sensor firmware, or may be separately disposed from the ambient light sensor 476 as a separate internal unit to the wearable computing device 400. The post-processed value representing the ambient light magnitude (e.g., a value in lux, rather than a raw signal) may be transmitted from the ambient environment brightness determination unit 480 to the one or more processors 450 and/or memory 460 for determining whether a current supplied to the light source (e.g., LED) 472*b* of the PPG sensor 472 should be adjusted.

The inertial sensors 474 (e.g., an inertial measurement unit) may measure motion data of the wearable computing device 400. The motion data may be transmitted to the one or more processors 450 and/or memory 460 for determining whether a current supplied to the light source (e.g., LED) 472*b* of the PPG sensor 472 should be adjusted. According to examples of the disclosure, the motion data may first pass through a motion data classifier 490 (e.g., a coarse classifier model) in order to understand or classify certain characteristics regarding the motion of the wearable computing device 400 (e.g., to determine and/or classify the motion as low, medium, high, periodic, aperiodic, etc.).

Figure 6:
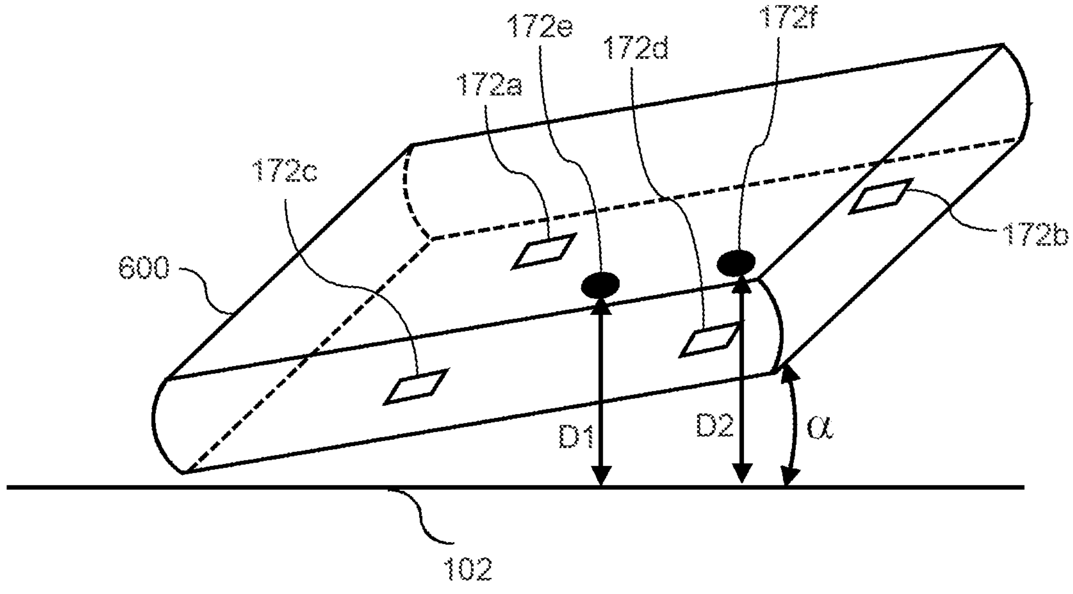
FIG. 6 illustrates an example wearable computing device spaced apart from a body part of a user, according to one or more example embodiments of the disclosure.

One or more detectors 472*a* of the PPG sensor 472 may also sense ambient light when a bottom side of the wearable computing device 400 is tilted or separated from the body part of the user. For example, the one or more detectors 472*a* may be configured to detect ambient light introduced to the one or more detectors 472*a* in a space between the lower part of the body of the wearable computing device 400 and the body part of the user, as shown in FIG. 6. The one or more processors 450 may be configured to adjust the current supplied to the one or more light sources (e.g. LEDs) 472*b* via LED driver 440, based on an amount of ambient light detected by the one or more detectors 472*a*.

The detectors 472*a* of the PPG sensor 472 may provide ambient light information (e.g., via a raw signal) relating to an ambient light condition to an analog-digital converter (ADC) 420 which converts one or more raw signals from the detectors 472*a* of the PPG sensor 472 into a value representing an ambient light magnitude (e.g., a lux value). The post-processed value representing the ambient light magnitude (e.g., a value in lux, rather than a raw signal) may be transmitted from the ADC 420 directly to the one or more processors 450 and/or memory 460 for determining whether a current supplied to the light source (e.g., LED) 472*b* of the PPG sensor 472 should be adjusted, or indirectly (e.g., via the analog front end (AFE) interface 410).

According to another example, the detectors 472*a* of the PPG sensor 472 may provide ambient light information (e.g., via a raw signal) to the ambient environment brightness determination unit 480 which converts one or more raw signals from the detectors 472*a* of the PPG sensor 472 into a value representing an ambient light magnitude (e.g., a lux value). This value may be transmitted from the ambient environment brightness determination unit 480 to the one or more processors 450 and/or memory 460 for determining whether a current supplied to the light source (e.g., LED) 472*b* of the PPG sensor 472 should be adjusted. Thus, the ambient environment brightness determination unit 480 may receive one or more raw signals from the one or more detectors 472*a* of the PPG sensor 472 as well as receive one or more raw signals from the ambient light sensor 476.

According to another example, an additional ambient environment brightness determination unit (not shown) may be provided to receive the one or more raw signals from the one or more detectors 472*a* of the PPG sensor 472. The post-processed value representing the ambient light magnitude (e.g., a value in lux, rather than a raw signal) sensed by the one or more detectors 472*a* of the PPG sensor 472 may be transmitted from the additional ambient environment brightness determination unit to the one or more processors 450 and/or memory 460 for determining whether a current supplied to the light source (e.g., LED) 472*b* of the PPG sensor 472 should be adjusted.

ADC 420 receives a PPG signal from the detectors 472*a* and converts the raw analog PPG signal to a digital signal. The analog front end (AFE) interface 410 is connected to the controller 470 and to the PPG sensor 472. The AFE interface 410 receives the digital signal from the ADC and transmits the digital signal to the one or more processors 150 and/or memory 460 of the controller 470, for measuring a biometric of the user (e.g., a heartrate). The AFE interface 410 may also be configured to communicate with the one or more processors 450 to control the LED driver 440. For example, the AFE interface 410 may relay information (e.g., a signal) from the one or more processors 450 to the LED driver 440 and/or a timing controller 430 to drive current to one or more LEDs **472*b* of the PPG sensor 472. The information may include a current value to be applied by the LED driver 440** and/or a timing of when to apply the current.

The PPG sensor 472 includes a timing controller 430 to, for example, control timing aspects for when the one or more LEDs **472*b* are to emit light, for when the one or more detectors 472*a*** are to receive light, and for when the ADC is to perform a conversion of the raw signal to the digital signal so that the PPG signal can be generated.

The PPG sensor 472 may also include various other components which are not shown for ease of description (e.g., filters to filter various components, such as noise, of the PPG signal). FIG. 4 illustrates by way of the dashed line that the ADC 420, timing controller 430, and LED driver 440 are part of the PPG sensor 472. However, one or more of the ADC 420, timing controller 430, and LED driver 440 may be separately disposed, for example as part of the AFE interface 410.

The memory 460 may be configured to store settings of the LED driver 440 and/or the one or more LEDs **472*b*, including a current setting of the one or more LEDs 472*b*, which acts as a reference point. In addition, the AFE interface 410 may also include a memory which stores settings of the LED driver 440 and/or the one or more LEDs 472*b*, including a current setting of the one or more LEDs 472*b*, which acts as a reference point. For example, the AFE interface 410 may have awareness of a current LED brightness setting (e.g., a current level currently supplied to the one or more LEDs 472*b*) and provide the current LED brightness setting to the one or more processors 450 for determining whether a current supplied to the one or more LEDs 472*b* should be adjusted. The one or more processors 450 use one or more of the inputs from the ambient light sensor 476, inertial sensors 474, and detectors 472*a*, as well as the current LED brightness setting, to determine whether a current supplied to the one or more LEDs 472*b* of the PPG sensor 472 should be adjusted. When the one or more processors 450 determine a brightness value needed for the one or more LEDs 472*b* to generate an accurate PPG signal is satisfied based on the current LED brightness setting, no adjustment may be made. Conversely, when the one or more processors 450 determine a brightness value needed for the one or more LEDs 472*b* to generate an accurate PPG signal can be satisfied by adjusting (e.g., lowering or increasing) the current LED brightness setting, the one or more processors 450 may control the LED driver 440 (e.g., via the AFE interface 410 and/or timing controller 430) to adjust an amount of current supplied to the one or more LEDs 472*b*, accordingly. After an updated brightness value is determined by the one or more processors 450, the one or more processors 450 may feed the updated brightness value back to the AFE interface 410 to adjust the brightness (i.e., the current) to the updated brightness value. For example, the one or more processors 450 may control the LED driver 440 (e.g., via the AFE interface 410 and/or timing controller 430) to increase or decrease a current supplied to the one or more LEDs 472*b*. For example, the one or more LEDs 472*b* may be driven at various current levels based on one or more of the inputs from the ambient light sensor 476, inertial sensors 474, and detectors 472*a***.

The LED brightness setting value (i.e., an amount of current to be supplied to the one or more LEDs **472*b***), may be obtained or determined by the one or more processors: (1) based on a lookup table derived from laboratory evaluations of optimal parameters, where ambient light values and motion data are the primary inputs; (2) based on a linear scaling (e.g., [motion+more ambient light]*scaling factor=new brightness value), where the scaling factor may be a value to ensure that the new brightness value does not exceed a capability of the LED; and/or (3) based on a nonlinear scaling, developed by training a machine learning model that leverages ambient light values and motion data as inputs and outputs an optimal LED brightness setting value (i.e., an amount of current to be supplied to the one or more LEDs **472*b*) given the environmental conditions. For example, the one or more processors 450 may control the LED driver 440 to increase an amount of current supplied to the one or more LEDs 472*b* to increase a brightness of the one or more LEDs 472*b* where the ambient light sensor 476 detects a brighter environment and/or where the inertial sensors 474 detect high movement of the wearable computing device 400**.

For example, the one or more LEDs **472*b* may be driven at a low setting (e.g., about 50 mA), a medium setting (e.g., about 100 mA), a high setting (e.g., about 200 mA), and a very high setting (e.g., about 250 mA). A low setting may be appropriate where the motion data indicates a user is stationary and an amount of ambient light detected is low (e.g., a lux value of 5,000 to 10,000 in outdoor conditions), a medium setting may be appropriate where the motion data indicates a user is stationary and an amount of ambient light detected is medium (e.g., a lux value of 10,001 to 30,000 in outdoor conditions), a high setting may be appropriate where the motion data indicates a user is moderately active and/or an amount of ambient light detected is high (e.g., a lux value of 30,001 to 65,000), and a very high setting may be appropriate where the motion data indicates a user is very active and/or an amount of ambient light detected is very high (e.g., a lux value of more than 65,000). However, the disclosure is not limited to these examples and other conditions may warrant different settings for the one or more LEDs 472*b***. In addition, the disclosure is not limited to the example LED current values and other values, e.g., intermediate values may be used, for example, as determined using a machine learning model. For example, the ambient lux values need not be categorized as low, medium, etc., and instead an actual determined lux value may be provided as an input to the machine learning model and a brightness value (i.e., current value) may be obtained from the model.

The PPG sensor 472 may optically measure biometric information such as a heart rate, using one or more light sources and one or more photodetectors at the surface of a user's body part to measure the volumetric variations of blood circulation. The light source (e.g., one or more LEDs) of the PPG sensor 472 emits light to a body part of a user and the photodetector of the PPG sensor 172, 472 measures the reflected light from the body part, where the amount of reflected light may indicate biometric information about the user (e.g., blood flow, volume of blood, etc.). The light source (e.g., one or more LEDs) may emit infrared light, and the color of the LED may be red, green, or yellow. The PPG signal may include various components, such as a DC component (or DC offset), which represents the constant absorption of light passing through the tissues, an AC component generated by heartbeats (cardiac activity) affecting blood volume, which depends on the systolic and diastolic phases, and an ambient light component which represents an amount of ambient light received by the detector (e.g., photodiode).

Figure 5A:
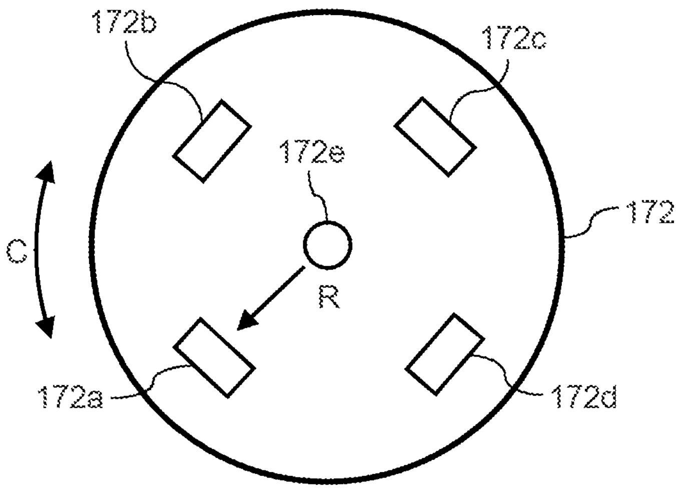
FIGS. 5A and 5B depict a bottom view of example wearable computing devices according to one or more example embodiments of the disclosure.

With reference to FIG. 5A, a bottom view of an example wearable computing device is illustrated according to one or more example embodiments of the disclosure. The wearable computing device may include a plurality of PPG sensors, for example to assist in rejecting motion artifacts. Each PPG sensor may correspond to a combination of one or more light sources and one or more detectors. For example, the wearable computing device may include two or more PPG sensors. Furthermore, more than one light source (e.g., a LED) may be included such that different detectors may be combined with different LEDs and/or each detector may be combined with one or more LEDs to output a respective PPG signal. For example, the plurality of detectors may be disposed in a circular or elliptical arrangement, where the plurality of detectors may be spaced apart from each other at regular or irregular intervals. In FIG. 5A, light source (e.g. LED) 172*e* is disposed in a central portion of the PPG sensor 172. Detector 172*a* is spaced apart from detectors 172*b* and 172*d* along a circumferential direction C, and is spaced apart from the light source (e.g. LED) 172*e* in a radial direction R. Likewise, each of detectors 172*b*, 172*c*, and 172*d* is spaced apart from adjacent detectors in the circumferential direction C, and is spaced apart from the light source (e.g. LED) 172*e* in a radial direction R. However, the configuration of the detectors and light source may be different from that illustrated in FIG. 5A, and the disclosure is not limited to the example of FIG. 5A.

Figure 5B:
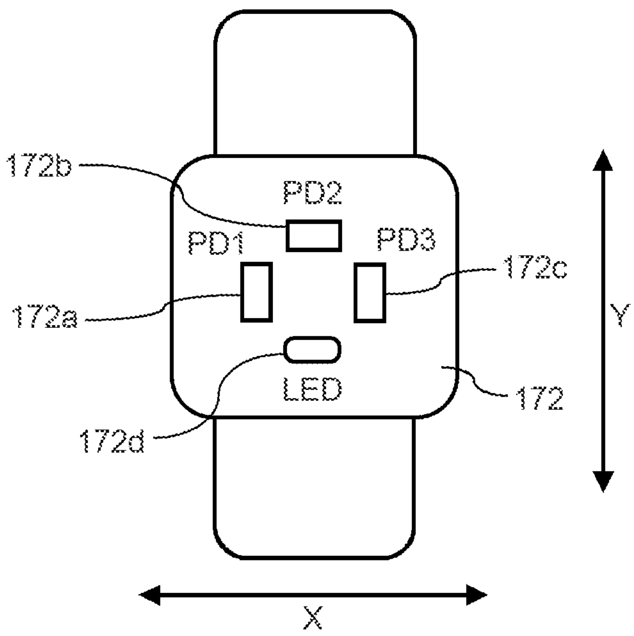

With reference to FIG. 5B, a bottom view of another example wearable computing device is illustrated according to one or more example embodiments of the disclosure. For example, in FIG. 5B detector 172*a* is spaced apart from detector 172*c* in the horizontal or "X" direction, and is spaced apart from detector 172*b* in both the horizontal (X) direction and the vertical or "Y" direction. Detector 172*b* is spaced apart from both detectors 172*a* and 172*c* in the horizontal (X) direction and vertical (Y) direction. Detector 172*c* is spaced apart from detector 172*a* in the horizontal (X) direction and is spaced apart from detector 172*b* in both the horizontal (X) direction and the vertical (Y) direction. Light source (e.g. LED) 172*e* is spaced apart from detector 172*b* in the vertical (Y) direction and is spaced apart from both detectors 172*a* and 172*c* in each of the horizontal (X) and vertical (Y) directions. However, the configuration of the detectors and light source may be different from that illustrated in FIG. 5B, and the disclosure is not limited to the example of FIG. 5B.

When a bottom side of the wearable computing device (and by extension the LED) is spaced apart from a body part by too great a distance, an amount of ambient light introduced between the bottom side of the wearable computing device and the body part of the user may interfere with the light emitted by the LED and/or the light received by the detector such that an accuracy of the PPG signal is degraded, or the distance from the LED to the body part of the user may be too far such that the PPG signal may not be accurate because the emitted light may not penetrate the body part sufficiently. Therefore, according to examples of the disclosure in such situations current to the LED may be cut off, for example to save energy.

With reference to FIG. 6, a side view of an example wearable computing device 600 is illustrated according to one or more example embodiments of the disclosure. For example, in FIG. 6, the wearable computing device 600 is displaced or spaced apart from a body part 102 of a user. The wearable computing device 600 includes a plurality of detectors (e.g., detectors 172*a*, 172*b*, 172*c*, and 172*d*) and a plurality of light sources (e.g., LEDs 172*e* and 172*f*). For example, when the wearable computing device 600 is spaced apart from the body part 102 of the user by more than a threshold amount (e.g., by more than the angle α), an LED which is spaced apart from the body part 102 by more than a distance d2 may be turned off (i.e., current supplied to the LED may be cut off), while an LED which is spaced apart from the body part 102 by less than a distance d2 may be kept on (i.e., current supplied to the LED may be maintained), and in an embodiment the current supplied to the LED may be increased (e.g., to a peak or maximum level). As another example, when the wearable computing device 600 is spaced apart from the body part 102 of the user by more than a threshold amount (e.g., by more than the angle α), a first LED which is spaced apart from the body part 102 by a distance which is greater than a distance that a second LED is spaced apart from the body part may be turned off (i.e., current supplied to the LED may be cut off), while the second LED may be kept on (i.e., current supplied to the second LED may be maintained), and in an embodiment the current supplied to the second LED may be increased (e.g., to a peak or maximum level). For example, the inertial sensors 174, 474 may include one or more of an accelerometer, a gyroscope, and a magnetometer to detect or sense motion data (e.g., a tilt angle, rate of movement, etc.) of the wearable computing device 100, 400. The motion data, such as the tilt angle, that is detected by the inertial sensors 174, 474 may be used to determine whether the wearable computing device 600 is spaced apart from the body part 102 of the user by more than the threshold amount.

For example, referring to FIG. 6, when the wearable computing device 600 is spaced apart from the body part 102 of the user by more than a threshold amount (e.g., by more than the angle α), and LED 172*f* is spaced apart from the body part 102 by more than distance d2, then power to LED 172*f* may be turned off (i.e., current supplied to the LED 172*f* may be cut off). However, LED 172*e*, which is spaced apart from the body part 102 by distance d1 which is less than a distance d2, may be kept on (i.e., current supplied to the LED 172*e* may be maintained), and in an embodiment the current supplied to the LED 172*e* may be increased (e.g., to a peak or maximum level).

As another example, when the wearable computing device 600 is spaced apart from the body part 102 of the user by more than a threshold amount (e.g., by more than the angle α), an LED which is farthest from the body part 102 may be turned off while one or more remaining LEDs may be kept on. In FIG. 6, LED 172*f* is spaced apart from the body part 102 by a distance d2 which is greater than a distance d1 that LED 172*e* is spaced apart from the body part 102. Therefore, the one or more processors may be configured to turn LED 172*f* off (i.e., current supplied to the LED 172*f* may be cut off), while the LED 172*e* may be kept on (i.e., current supplied to the LED 172*e* may be maintained), and in an embodiment the current supplied to the LED 172*e* may be increased (e.g., to a peak or maximum level).

According to one or more examples of the disclosure, one or more motion signals generated by one or more inertial sensors (e.g., inertial sensors 174, 474 as in FIGS. 3 and 4) may indicate at least part of a bottom side of the wearable computing device 100, 400 is spaced apart from a body part 102 of the user (e.g., by a predetermined distance or by a predetermined angle). The one or more processors 150, 450 may be configured to cut off current supplied to the at least one of the LEDs (e.g., one or more of the LEDs which are located on a side of the wearable computing device 100, 400 that is most spaced apart from the body part 102 of the user), and to increase current supplied to one or more remaining LEDs (e.g., one or more LEDs which are located on a side of the wearable computing device 100, 400 which remains in contact with the body part 102 of the user or is closest to the body part 102 of the user). For example, the one or more processors 150, 450 may determine at least part of a bottom side of the wearable computing device 100, 400 is not in contact with the body part 102 of the user based on a tilt angle of the wearable computing device 100, 400 detected by the inertial sensors 174, 474 and/or based on a movement of the wearable computing device 100, 400. In one or more examples, the inertial sensors 174, 474 may include one or more of an accelerometer, a gyroscope, and a magnetometer to detect or sense motion data (e.g., a tilt angle, rate of movement, etc.) of the wearable computing device 100, 400.

When a bottom side of the wearable computing device (and by extension the LED) is spaced apart from a body part in some instances accuracy of a PPG signal can be maintained or sufficient for measurement purposes by increasing power (current) to one or more LEDs. That is, the distance from the LED to the body part of the user may not be too far such that the PPG signal may be accurate or acceptable because the emitted light may penetrate the body part sufficiently. In an embodiment of the disclosure, a wearable computing device may include a plurality of light sources (e.g., LEDs) where at least one of the light sources is turned off while at least one light source is turned on. If one or more motion signals generated by one or more inertial sensors 174, 474 indicate at least part of a bottom side of the wearable computing device 100, 400 is spaced apart from a body part 102 of the user (e.g., by less than a predetermined distance or by less than a predetermined angle), the one or more processors 150, 450 may be configured to turn on power supplied to the at least one of the light sources which is turned off. In addition, current may be increased to the one or more light sources which were previously turned on (e.g., to peak value or maximum level).

Figure 7:
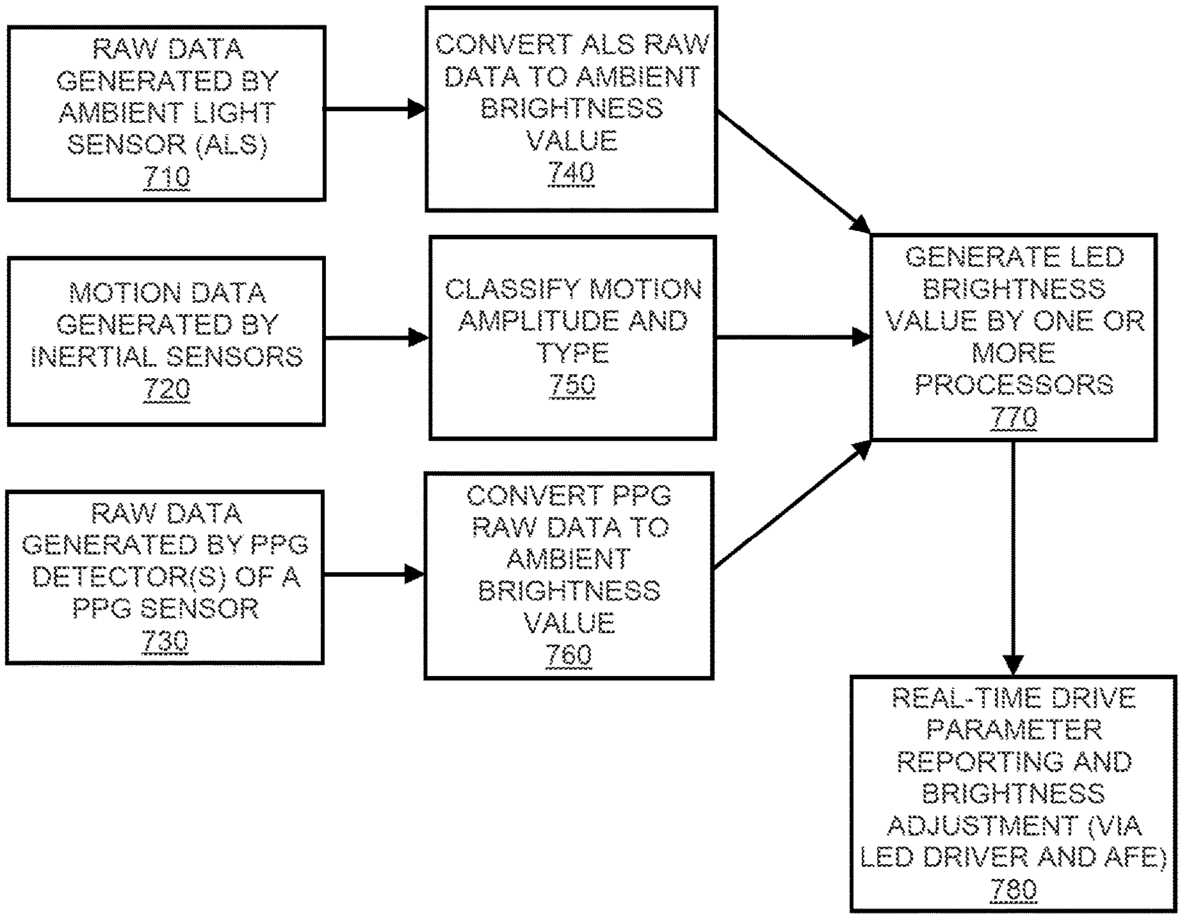
FIG. 7 illustrates a flow diagram for adjusting a brightness value based on one or more inputs, according to one or more example embodiments of the disclosure.

Referring to FIG. 7, a flow diagram for adjusting a brightness value based on one or more inputs is illustrated, according to one or more example embodiments of the disclosure. The flow diagram FIG. 7 is another illustration which explains operations of a wearable computing device which may include any of the wearable computing devices described herein. As previously explained and as illustrated at operation 710, one or more ambient light sensors of the wearable computing device may detect an amount of ambient light in a surrounding environment of the wearable computing device. The one or more ambient light sensors may be disposed in an upper part of the body of the wearable computing device below a display, and detect ambient light through a transparent display panel (cover).

At operation 720, one or more inertial sensors (e.g., an accelerometer, magnetometer, gyroscope, etc.) of the wearable computing device may detect movement of the wearable computing device (e.g., a tilt angle of the wearable computing device, velocity, angular velocity, acceleration, angular acceleration, orientation information, and the like), and generate motion data.

At operation 730, one or more PPG detectors of a PPG sensor may generate raw data which indicates an ambient light condition in a surrounding environment of the wearable computing device. For example, the one or more processors may control (e.g., via one or more of a timing controller, AFE interface, and LED driver) for the LEDs of the PPG sensor to be turned off so as to obtain a measurement of light received by the PPG detectors while the LEDs are turned off, to more easily assess an ambient light condition.

At operation 740, the ALS raw data may be converted to an ambient brightness value (e.g., a lux value).

At operation 750, the motion data may be classified, for example according to an amplitude of the motion and a type of the motion. For example, the motion may be classified according to rates of acceleration. The motion data may also be used to describe or infer a state of the user wearing the wearable computing device (e.g., stationary, walking, running, climbing steps, swimming, etc.). For example, the classifier model may classify the motion as low, medium, high, periodic, aperiodic, etc.

At operation 760, the PPG raw data may be converted to an ambient brightness value (e.g., a lux value).

At operation 770, the one or more processors receive as inputs one or more of the ambient brightness value obtained via the ALS, and optionally also the ambient brightness value obtained via the PPG detectors and motion information obtained from the inertial sensors. The one or more processors may generate one or more LED brightness values according to the inputs and adjust a current of one or more LEDs of the PPG sensor via one or more of an AFE interface, LED driver, and timing controller.

For example, the one or more processors may determine whether to adjust a current of the one or more LEDs on an ad hoc basis, or according to a predetermined schedule (e.g., every few seconds). For example, the one or more processors may determine whether to adjust a current of the one or more LEDs at the same time as determining whether to adjust a brightness of the display.

At operation 780, the LED driver may adjust the current supplied to the one or more LEDs of the PPG sensor according to the control of the one or more processors. A real-time value of the current applied to the one or more LEDs may be reported by the AFE interface to the one or more processors as a reference point.

Figure 8:
FIG. 8 illustrates a flow diagram of an example, non-limiting computer-implemented method according to one or more example embodiments of the disclosure.
Figure 8:
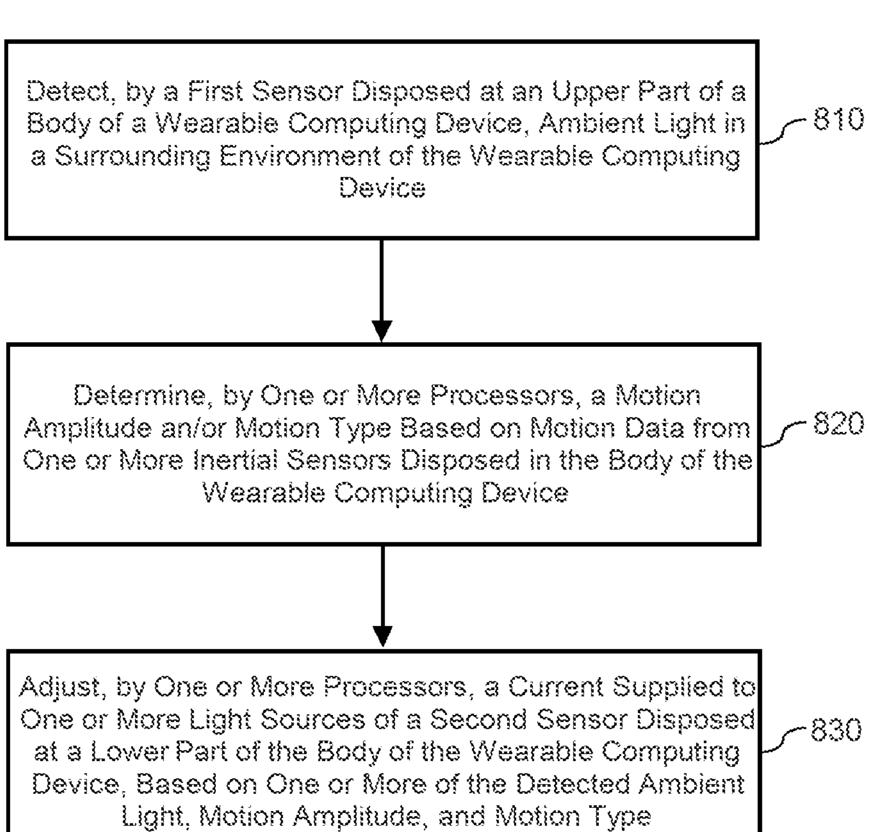

Examples of the disclosure are also directed to computer implemented methods of a wearable computing device. FIG. 8 illustrates a flow diagram of an example, non-limiting computer-implemented method 800 according to one or more example embodiments of the disclosure. The features of the method 800 may be implemented by any of the wearable computing devices described herein, including wearable computing device 100 discussed above with reference to FIG. 1, wearable computing device 400 discussed above with reference to FIG. 4, and wearable computing device 600 discussed above with reference to FIG. 6.

At (810), the method 800 includes detecting, by a first sensor (e.g., ALS 176) disposed at an upper part of a body of a wearable computing device (e.g., upper part 110*a* of a body 110 of the wearable computing device 100), ambient light in a surrounding environment of the wearable computing device. At (820), the method 800 includes determining, by one or more processors of the wearable computing device, a motion amplitude of the wearable computing device and/or a motion type of the wearable computing device based on motion data generated by one or more inertial sensors device (e.g., inertial sensors 174 of the wearable computing device 100) disposed in the body of the wearable computing device. At (830), the method 800 includes adjusting, by the one or more processors, a current supplied to one or more light sources of a second sensor (e.g., one or more LEDs of PPG sensor 172 of the wearable computing device 100) based on one or more of the detected ambient light, the determined motion amplitude, and the determined motion type. The second sensor (e.g., PPG sensor 172) may be disposed at a lower part of the body of the wearable computing device (e.g., lower part 110*b* of the body 110 of the wearable computing device 100) and includes one or more light sources which emit light toward a body part of a user when the wearable computing device is worn by the user and one or more detectors which receive a reflection of the light emitted toward the body part to generate a signal indicating a biometric of the user.

Aspects of the above-described example embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks, Blue-Ray disks, and DVDs; magneto-optical media such as optical discs; and other hardware devices that are specially configured to store and perform program instructions, such as semiconductor memory, read-only memory (ROM), random access memory (RAM), flash memory, USB memory, and the like. Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the non-transitory computer-readable storage media may also be embodied in at least one application specific integrated circuit (ASIC) or Field Programmable Gate Array (FPGA).

Each block of the flowchart illustrations may represent a unit, module, segment, or portion of code, which comprises one or more executable instructions for implementing the specified logical function(s). It should also be noted that in some alternative implementations, the functions noted in the blocks may occur out of order. For example, two blocks shown in succession may in fact be executed substantially concurrently (simultaneously) or the blocks may sometimes be executed in the reverse order, depending upon the functionality involved.

While the disclosure has been described with respect to various example embodiments, each example is provided by way of explanation, not limitation of the disclosure. Those skilled in the art, upon attaining an understanding of the foregoing, can readily produce alterations to, variations of, and equivalents to such embodiments. Accordingly, the disclosure does not preclude inclusion of such modifications, variations and/or additions to the disclosed subject matter as would be readily apparent to one of ordinary skill in the art. For example, features illustrated or described as part of one embodiment can be used with another embodiment to yield a still further embodiment. Thus, it is intended that the disclosure covers such alterations, variations, and equivalents.

What is claimed is:

1. A wearable computing device, comprising:

a body;

a first sensor, disposed at an upper part of the body, configured to detect an amount of ambient light in a surrounding environment of the wearable computing device;

one or more processors configured to adjust a current supplied to one or more light sources based on the amount of ambient light detected by the first sensor; and a second sensor, disposed at a lower part of the body, the second sensor including the one or more light sources and one or more detectors, the one or more light sources being configured to emit light based on the adjusted current toward a body part of a user when the wearable computing device is worn by the user and the one or more detectors being configured to receive a reflection of the light emitted toward the body part to generate a signal indicating a biometric of the user.

2. The wearable computing device according to claim 1, wherein the second sensor includes a photoplethysmography (PPG) sensor configured to monitor a heart rate of the user when the wearable computing device is worn by the user, the one or more light sources include one or more light-emitting diodes, and the one or more detectors include one or more photodiodes.

3. The wearable computing device according to claim 1, further comprising:

one or more inertial sensors, disposed in the body, configured to generate one or more motion signals based on a movement of the wearable computing device, wherein the one or more processors are configured to adjust the current supplied to the one or more light sources based on the one or more motion signals generated by the one or more inertial sensors.

4. The wearable computing device according to claim 3, wherein the one or more processors are configured to increase the current supplied to the one or more light sources in response to the one or more motion signals generated by the one or more inertial sensors indicating a motion of the wearable computing device is of a predetermined type or is greater than a threshold value.

5. The wearable computing device according to claim 3, wherein the second sensor includes a photoplethysmography (PPG) sensor configured to monitor a heart rate of the user when the wearable computing device is worn by the user, the one or more light sources include a plurality of light-emitting diodes, the one or more detectors include a plurality of photodiodes, and when the one or more motion signals generated by the one or more inertial sensors indicate the lower part of the body of the wearable computing device is spaced apart from the body part of the user, the one or more processors are configured to cut off current supplied to at least one of the plurality of light-emitting diodes, and to increase current supplied to at least one other light-emitting diode of the plurality of light-emitting diodes.

6. The wearable computing device according to claim 1, wherein the one or more processors are configured to increase the current supplied to the one or more light sources in response to the amount of ambient light detected by the first sensor being greater than a threshold value.

7. The wearable computing device according to claim 1, further comprising:

one or more inertial sensors, disposed in the body, configured to generate one or more motion signals based on a movement of the wearable computing device, wherein the one or more processors are configured to increase the current supplied to the one or more light sources if the amount of ambient light detected by the first sensor is greater than a first threshold value and the one or more motion signals generated by the one or more inertial sensors indicate a motion of the wearable computing device is of a predetermined type or is greater than a second threshold value.

8. The wearable computing device according to claim 1, further comprising:

a display, disposed at the upper part of the body of the wearable computing device, configured to display biometric information, wherein:

the first sensor includes an ambient light sensor disposed beneath the display, and the ambient light sensor has a first sampling rate to detect the amount of ambient light in a first operating mode of the wearable computing device, and a second sampling rate to detect the amount of ambient light in a second operating mode of the wearable computing device.

9. The wearable computing device according to claim 1, wherein the one or more detectors are configured to detect ambient light in a space between the lower part of the body of the wearable computing device and the body part of the user, and the one or more processors are configured to adjust the current supplied to the one or more light sources based on an amount of ambient light detected by the one or more detectors.

10. The wearable computing device according to claim 1, wherein the one or more processors are configured to determine a current value for which the current is to be adjusted to, according to one or more of a lookup table, a linear scaling method, and a nonlinear scaling method, using the amount of ambient light detected by the first sensor as an input.

11. A computer-implemented method, comprising:

detecting, by a first sensor disposed at an upper part of a body of a wearable computing device, an amount of ambient light in a surrounding environment of the wearable computing device;

adjusting, by one or more processors, a current supplied to one or more light sources of a second sensor based on the amount of ambient light detected by the first sensor, wherein the second sensor is disposed at a lower part of the body and includes the one or more light sources and one or more detectors;

emitting, by the one or more light sources of the second sensor and based on the adjusted current, light toward a body part of a user when the wearable computing device is worn by the user; and receiving, by the one or more detectors of the second sensor, a reflection of the light emitted toward the body part to generate a signal indicating a biometric of the user.

12. The computer-implemented method of claim 11, further comprising:

generating, by one or more inertial sensors disposed in the body of the wearable computing device, one or more motion signals based on a movement of the wearable computing device, wherein adjusting, by the one or more processors, the current supplied to the one or more light sources of the second sensor, is further based on the one or more motion signals generated by the one or more inertial sensors.

13. The computer-implemented method of claim 12, further comprising:

in response to the one or more motion signals generated by the one or more inertial sensors indicating a motion of the wearable computing device is of a predetermined type or is greater than a threshold value, increasing the current supplied to the one or more light sources.

14. The computer-implemented method of claim 12, wherein the second sensor includes a photoplethysmography (PPG) sensor configured to monitor a heart rate of the user when the wearable computing device is worn by the user, the one or more light sources include a plurality of light-emitting diodes, and the one or more detectors include a plurality of photodiodes, the method further comprising:

in response to the one or more motion signals generated by the one or more inertial sensors indicating the lower part of the body of the wearable computing device is spaced apart from the body part of the user, cutting off current supplied to at least one of the plurality of light-emitting diodes, and increasing current supplied to at least one other light-emitting diode of the plurality of light-emitting diodes.

15. The computer-implemented method of claim 12, further comprising:

detecting, by the one or more detectors, ambient light in a space between the lower part of the body of the wearable computing device and the body part of the user, and adjusting, by the one or more processors, the current supplied to the one or more light sources of the second sensor, is further based on an amount of ambient light detected by the one or more detectors.

16. The computer-implemented method of claim 15, further comprising:

determining, by the one or more processors, a current value for which the current is to be adjusted to, according to one or more of a lookup table, a linear scaling method, and a nonlinear scaling method, using one or more of the amount of ambient light detected by the first sensor, the amount of ambient light detected by the one or more detectors, and the one or more motion signals generated by the one or more inertial sensors.

17. The computer-implemented method of claim 11, further comprising:

generating, by one or more inertial sensors disposed in the body, one or more motion signals based on a movement of the wearable computing device; and increasing the current supplied to the one or more light sources to a peak value when the amount of ambient light detected by the first sensor is greater than a first threshold value and the one or more motion signals generated by the one or more inertial sensors indicate a motion of the wearable computing device is of a predetermined type or is greater than a second threshold value.

18. The computer-implemented method of claim 11, further comprising:

displaying, on a display of the wearable computing device, biometric information, wherein the first sensor is an ambient light sensor disposed below the display, and detecting the amount of ambient light by the ambient light sensor includes sampling the ambient light at a first sampling rate in a first operating mode of the wearable computing device, and at a second sampling rate in a second operating mode of the wearable computing device.

19. A non-transitory computer-readable medium which stores instructions that are executable by one or more processors of a wearable computing device, the instructions comprising:

instructions to cause the one or more processors to receive information indicating an amount of ambient light in a surrounding environment of the wearable computing device detected by a first sensor disposed at an upper part of a body of the wearable computing device;

instructions to cause the one or more processors to adjust a current supplied to one or more light sources of a second sensor based on the amount of ambient light detected by the first sensor, wherein the second sensor is disposed at a lower part of the body and includes the one or more light sources and one or more detectors;

instructions to cause the one or more light sources of the second sensor to emit, based on the adjusted current, light toward a body part of a user when the wearable computing device is worn by the user; and instructions to cause the one or more detectors to receive a reflection of the light emitted toward the body part to generate a signal indicating a biometric of the user.

20. The non-transitory computer-readable medium of claim 19, the instructions further comprising:

instructions to cause the one or more processors to receive information indicating a type of motion of the wearable computing device and/or an amplitude of movement of the wearable computing device, based on one or more motion signals generated by one or more inertial sensors disposed in the body of the wearable computing device; and the instructions to cause the one or more processors to adjust the current supplied to the one or more light sources is further based on the information indicating the type of motion of the wearable computing device and/or the amplitude of movement of the wearable computing device.

* * * * *